United States Patent [19]

Lai et al.

[11] 4,066,512

[45] Jan. 3, 1978

[54] BIOLOGICALLY ACTIVE MEMBRANE MATERIAL

[75] Inventors: Chung Jung Lai, Watertown; Stanley M. Goldin, Norwood, both of Mass.

[73] Assignee: Millipore Corporation, Bedford, Mass.

[21] Appl. No.: 684,746

[22] Filed: May 10, 1976

Related U.S. Application Data

[63] Continuation of Ser. No. 503,624, Sept. 6, 1974, abandoned.

[51] Int. Cl.$^2$ .................... C07G 7/00; C07G 7/02; G01N 31/14
[52] U.S. Cl. ........................................ 195/127; 195/63; 195/103.5 R; 195/103.5 A; 195/103.5 Y; 260/6; 260/112 R; 424/2
[58] Field of Search .................. 195/63, 68, DIG. 11, 195/103.5 R, 127; 424/94, 2; 427/338, 414, 439; 260/2.5 A, 6

[56] References Cited

U.S. PATENT DOCUMENTS

| 2,930,736 | 3/1960 | Sullivan et al. | 195/68 X |
| 3,322,632 | 5/1967 | Schwick et al. | 424/94 X |
| 3,705,084 | 12/1972 | Reynolds | 195/63 |
| 3,758,396 | 9/1973 | Vieth et al. | 195/68 X |
| 3,809,613 | 5/1974 | Vieth et al. | 195/63 |
| 3,843,446 | 10/1974 | Vieth et al. | 195/68 |
| 3,865,548 | 2/1975 | Padamer | 195/127 X |

OTHER PUBLICATIONS

Olson, et al., Immobilized Enzymes in Food and Microbial Processes, Plenum Press N.Y. 8/1974, (pp. 157–168, 176–178 & 181–182).

Goldman, et al., Papain Membrane on a Collodion Matrix, Science, vol. 150, 1965, (pp. 758–760).

Thong, et al., Observations on the Activity of Enzymes after Filtration on (and through) a Nitrocellulose Membrane, Biochemical and Biophysical Res. Comm., vol. 31, 1968 (pp. 1–8).

Wheeler, et al., Properties of two Phosphatases, Attached to Insoluble Cellulose Matrices; Biochim. Biophys. Acta. vol. 191, 1969 (pp. 187–189).

Zaborsky, O., Immobilized Enzymes, CRC Press, Chemical Rubber Co., Cleveland, Ohio, 1973 (pp. 73, 80, 83, 130–132, 151 & 158).

*Primary Examiner*—David M. Naff

[57] ABSTRACT

A composite membrane structure for immobilizing biologically active materials, such as enzymes, is formed by coating a microporous polymeric membrane with a thin layer of an inert proteinaceous material, such as zein or collagen, so that the resultant coated membrane retains intercommunicating capillary pores that extend through its structure. Immobilization of a biologically active material is carried out by contacting the coated membrane with the biologically active material in solution and drying. Biologically active materials immobilized on the membrane can be used to perform biochemical reactions and are useful in carrying out tests for glucose and uric acid.

18 Claims, 5 Drawing Figures

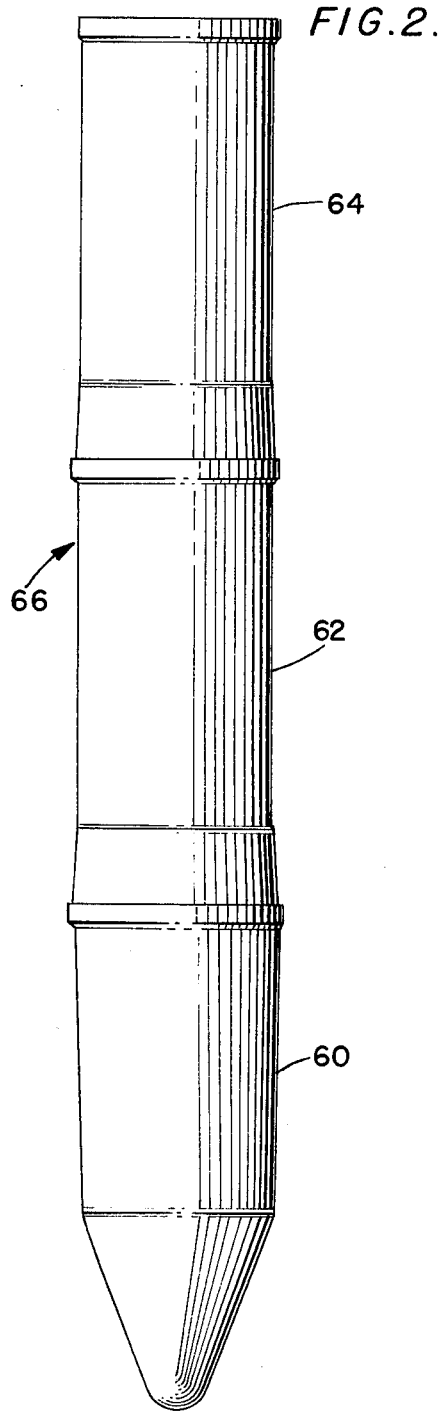
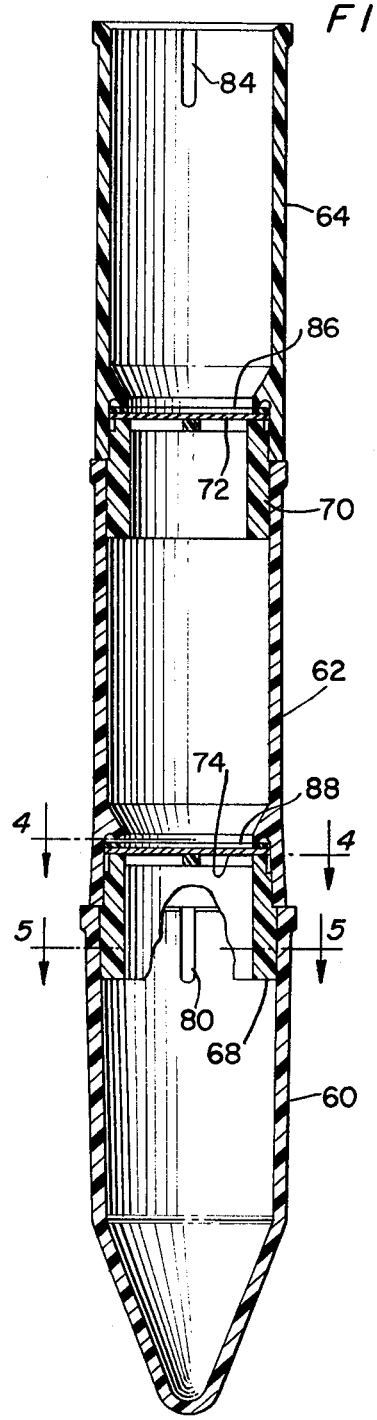
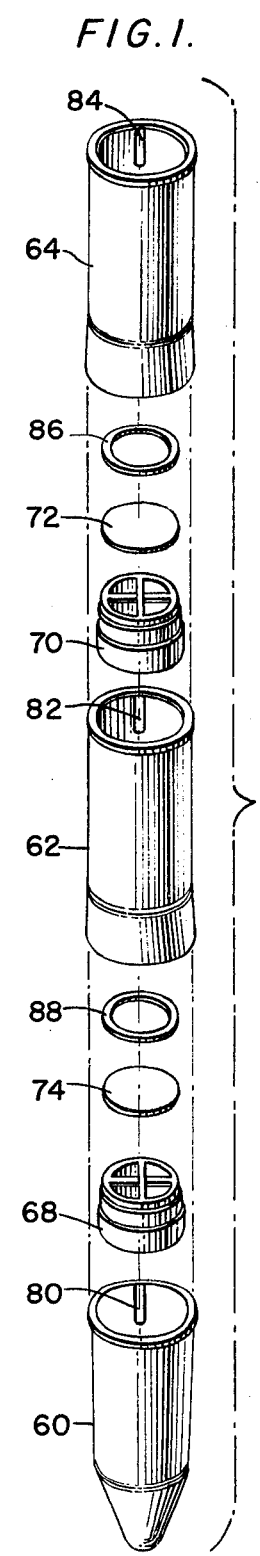
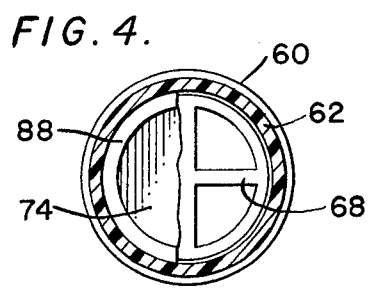
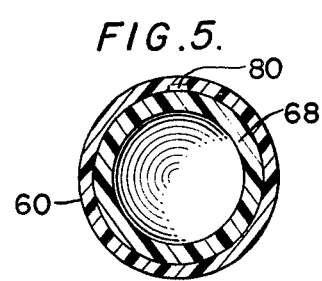

BIOLOGICALLY ACTIVE MEMBRANE MATERIAL

This is a continuation, of application Ser. No. 503,624 filed Sept. 6, 1974, now abandoned.

BACKGROUND OF THE INVENTION

The field of the present invention is catalytic filters. More specifically, the present invention is directed to a polymeric microporous matrix to which a biologically active agent such as an enzyme or an antibody is applied to perform the catalysis as reactive materials come in contact with the matrix either by bulk flow or by diffusion.

The polymeric microporous matrix will sometimes be referred to herein as a microporous membrane filter, since such materials have found wide usage for filtration.

It is well known that enzymes can function as catalysts for certain biochemical reactions. However, the recovery of enzymes from solutions into which they have been introduced to act as a catalyst is often complex and difficult. A further problem associated with the use of enzymes as catalysts is that enzymes have a relatively short shelf life. This short shelf life is significant because enzymes are often extremely expensive and difficult to obtain, particularly in high purity.

It is known that the recovery problem is significantly reduced if the enzyme is bound to the surface of an insoluble substance. With an enzyme bound to such a surface, the solution containing the reactants for which the enzyme is a catalyst is then passed over the surface to which the enzyme is bound to allow the enzyme to catalyse a reaction. Since the enzyme is bound, with this procedure, it remains in place and its recovery from the reactive solution is not required.

One known method for binding an enzyme to a surface is to use a film-like non-porous carrier which is capable of complexing and binding to enzymes so that enzymatic reactions can be effected by passing reactants over the membrane or film. In this known prior art procedure, enzymes are bound to or immobilized on a thin protein membrane formed of a protein such as collagen or zein. The particular enzyme is bound to the membrane after the membrane is swollen with a weak acid. The foregoing procedure for catalysing reactions with bound enzymes has a number of deficiencies, the most significant of which is that with such non-porous films the amount of catalyst which can be bound per unit volume is low as compared with the amount which can be bound per unit volume with the structure of the present invention. Thus much more of the prior non-porous structure is required to obtain a given catalytic capacity.

SUMMARY OF THE INVENTION

The amount of catalytic surface that is exposed to reactants is significantly increased with the biologically active porous membrane material of the present invention in which the biologically active agent or catalyst is bound with a protein to a highly microporous polymeric material.

Accordingly, it is an object of the present invention to provide an inert polymeric material to which a biologically active agent is bound and which permits the passage of reactants therethrough.

Another object of the present invention is to provide a microporous polymeric membrane to which an enzyme is bound and which promotes contact between the enzyme and reactants when reactants flow through the membrane.

A further object of the present invention is to provide an enzyme coated polymeric substrate through which a reactive material can pass and be catalyzed.

A further object of the invention is to provide a novel column containing a biologically active agent immobilized on a polymeric microporous matrix.

BRIEF DESCRIPTION OF THE DRAWINGS

FIG. 1 is an exploded perspective view of an enzyme column in accordance with the present invention;

FIG. 2 is an elevational view, on a larger scale, of an enzyme column in accordance with the present invention;

FIG. 3 is a view similar to FIG. 2 but in section and partially broken away;

FIG. 4 is a sectional view taken along the line 4—4 of FIG. 3; and,

FIG. 5 is a sectional view taken along the line 5—5 of FIG. 3.

DESCRIPTION OF THE PREFERRED EMBODIMENTS

At the outset, the invention is described in its broadest aspects with a more detailed description following. In its broadest aspects, the invention is a catalytic material which includes a substrate which is a microporous polymeric membrane matrix to which a biologically active agent is bound. The active agent is bound to the porous polymeric matrix with an inert protein.

Filter membranes which can be employed as substrates for the biologically active agents are widely known and may be prepared in accordance with the procedure disclosed in U.S. Pat. No. 1,421,341 to Zsigmondy et al., entitled "Filter and Method of Producing Same," and U.S. Pat. No. 2,783,894, to Lovell et al., entitled "Microporous Nylon Film," the teachings of which patents are incorporated herein by reference. Such membranes are used to perform removal of particles from fluids with a high degree of precision, at high levels of flux through the membrane. Few if any other separatory materials offer so wide a range of potential applications, since it is limited only by the list of macromolecular solutes that may be of interest in a specific situation. Sterilizing filtration of biological materials, filtration of hydraulic fluids to remove particulate materials therefrom and collection of bacteria for water analysis are typical uses.

The membrane filters used as the substrate of the biologically active agents of the present invention are thin porous structures composed of pure and biologically inert cellulose esters or similar polymeric materials. They are produced commercially in many distinct pore sizes, from 14 micrometers to 25 nanometers (0.025 micrometer), and in discs ranging from 13 to 293 mm in diameter. They can of course, be shaped in any desired configuration.

The pores in these membrane filters are extraordinarily uniform in size. For example, the total range of pore size distribution in one commercially available membrane filter with a mean pore size of 0.45 micrometers is plus or minus 0.02 micrometer. Each square centimeter of membrane filter surface contains millions of capillary pores which occupy approximately 80 percent of the total filter volume.

As is set forth above, the biologically active agent is bound to the porous polymeric filter by a material such as a water insoluble protein. Two useful inactive proteins for binding enzymes and antibodies to the polymeric membrane are zein and collagen.

Zein is the prolamin (alcohol-soluble protein) of corn. It is the only commercially available prolamin and one of the few readily available plant proteins. Zein occurs primarily in the endosperm of the corn kernel. The amount of alcohol-soluble protein is directly related to the total endosperm protein content, with zein contents ranging from 2.2 to 10.4 percent of the dry substance in various corn sample.

Zein is characterized by a relative deficiency of hydrophilic groups in comparison with most proteins. In fact, the high proportion of nonpolar (hydrocarbon) and acid amide side chains accounts for the solubility of zein in organic solvents and its classification as a prolamin.

One of the commercial zeins is Argo Zein G-200, manufactured by Corn Products Refining Company, Argo, Illinois.

Collagen is a hydroxproline, glycine-type protein, which is the chief organic constituent of connective animal tissue and bones. It can be obtained in good yields from a wide variety of mammal and fish parts, and is frequently obtained from pork, sheep and beef tendons; pigskins; tanner's stock, which are calfskins not usable for leather; and ossein, which is tissue obtained by drying cattle bones remaining after acid treatment to remove calcium phosphate.

Although collagen and zein are preferred materials for binding the enzyme to the polymeric matrix, other proteins and polypeptides are usable. Other non-limiting examples of suitable water insoluble natural proteins include fibrinogen, keratins, glutelins, and the like. Non-limiting examples of suitable synthetic polypeptides include polyisoleucine, polytryptophan, polyphenylalanine, polytyrosine, and copolymers of leucine with p-amino phenylalanine. Certain water soluble proteins which can be treated to render them water-insoluble may also be used for binding the enzymes.

The selection of a particular synthetic polypeptide or natural protein, in modified or unmodified form, will be largely determined by the nature of the enzyme (or antibody) and the reaction environment to be encountered. Because of their inertness to a large number of enzymes, collagen and zein are preferred natural protein materials.

A wide variety of different types of enzymes can be bound to polymeric filter membranes with natural proteins such as collagen and zein. For instance, suitable enzymes include amylases, lysozyme, invertase, urease, uricase, celluloses, catecholmethyltransferase, sucrose 6-glucosyl-transferase, hexokinase, carboxyl esterase, D Nase, aryl esterase, lipase, pectin esterase, glucoamylase, amylopectin-1, 6-glucosidase, oligo-1, 6-glucosidase, polygalacturonase, $\alpha$-glucosidase, $\beta$-glucosidase, $\beta$-galactosidase, glucose oxidase, galactose oxidase, catechol oxidase, catalase, peroxidase, lipoxidase, glucose isomerase, pentosanases, cellobiase, xylose isomerase, sulphite oxidase, ethanolamine oxidase, penicillinase, carbonic anhydrase, gluconolactonase, 3-keto steroid $\Delta$ ' dehydrogenase, 11-$\beta$-hydroxylase, amino acid acylases and glucose-6-phosphate dehydrogenase. Compatible combinations of enzymes and multi-enzyme systems can also be complexed with the collagen in this manner. Examples include hexokinase with glucose-6-phosphate dehydrogenase and hexokinase with glucose oxidase.

Especially suitable, however, are lysozyme, invertase, urease and amylases. Lysozyme is widely used to hydrolyze micro-organisms in pharmaceutical research and in sewage treatment, either alone or in combination with other enzymes and/or bacteria. One particularly important application for lysozyme-protein membrane complex is in the lysis of cells.

Invertase or $\beta$-D-fructofuranosidase is widely used in the food and beverage industries, as well as for analytical purposes. Invertase can be used to catalyse the hydrolysis of sucrose to glucose and fructose or invert sugar. Invertase is effective in the hydrolysis of $\beta$-D-fructofuranosyl linkages in sucrose, raffinose, gentianose, and methyl and $\beta$-fructofructose. One particularly important application for an invertase-protein membrane complex is in the continuous hydrolysis of sucrose.

Urease is a highly specific enzyme which can catalyze the transformation of urea to ammonium carbonate, and is often used to determine the urea content in urine specimens. Because of its highly specific activity, one utility for the urease-protein complex membrane is in kidney machine applications. More particularly, urease-protein complex membranes can be used for repeated hydrolysis of urea, such as in the treatment of human wastes. $\alpha$-amylase is referred to as the "liquifying enzyme" and is known to randomly hydrolyze starch, glycogen, and dextrans. $\beta$-amylase can produce maltose from sugar, glycogen and dextran. Other suitable amylases include $\alpha$-glucosidase, amyloglucosidase, amylo-1, 6-$\alpha$-glucosidase (debranching enzyme), obligo-1, 6-glucosidase (limit dextrinase), isomaltase, and isotriase. As used herein, the term "amylase" refers generically to one or more of these and other amylases. One particularly important application of the amylase-protein complex of the present invention is in the continuous passage of starch substrates over the enzymatically active membrane to effect continuous hydrolysis of starch.

Several enzymes can be simultaneously complexed with the protein membrane. For instance, it is quite desirable to complex $\alpha$-amylase with other types of enzymes, since $\beta$-amylase is capable of randomly cleaving a starch molecule, so as to provide reactive sites for other more specific enzymes.

Procedures for coating an inert protein on to a microporous polymeric membrane in accordance with the present invention are set forth in Examples 1 an 2 below. At this point, it should be noted that the invention is not intended to be limited to the procedures set forth in the examples which follow, but rather these examples are provided in order to teach one skilled in the art how to practice the invention and thus are not intended to limit the invention in any way.

EXAMPLE 1

A zein solution was prepared by admixing 18 cc of ethanol, 34 cc of n-butanol, 8 cc of water, 3 cc of cellusolve solvent, and 7.9 grams of zein. The zein dissolves readily in the foregoing solvents and the solution can be prepared at room temperature (20° C). The solution is mixed for a sufficient amount of time to enable all the zein to be dissolved therein.

Thereafter, a microporous polymeric filter is soaked in the zein solution. A filter known as type "SS" filter sold by the Millipore Corporation, Bedford, Massachusetts which has an average pore size of 3.0 micrometers was used. The singular remained in the solution for approximately 24 hours at room temperature. The coated filter is then air dried.

stacks of filters were washed thoroughly with 50 cc of water between each run. The results are summarized below:

| No. of run | 1 | | | 2 | | | 3 | | | 4 | | | 5 | | |
|---|---|---|---|---|---|---|---|---|---|---|---|---|---|---|---|
| Approx. residence time | 9 sec | 18 sec | 24 sec | 9 sec | 18 sec | 24 sec | 9 sec | 18 sec | 24 sec | 9 sec | 18 sec | 24 sec | 9 sec | 18 sec | 24 sec |
| % conv. | 92 | 92 | 77 | 46 | 80 | | 30.7 | 50 | 85 | 30.7 | 50 | 72 | 34.5 | 46 | 77 |

EXAMPLE 2

A collagen coated filter is prepared from a collagen solution consisting of 0.7 grams of acid soluble collagen in 80 ml. of 0.1 N acetic acid. A microporous polymeric membrane filter is soaked in the collagen solution for about 24 hours. Prior to being complexed with an enzyme or an antibody, the collagen-coated filter is then air dried.

The procedure for complexing a biologically active agent such as an enzyme on to the protein-coated polymeric filter is quite simple. After the protein coated filter has been prepared for complexing in accordance with the procedure set forth above, the protein-coated filter is contacted with a solution of the enzyme for a period of approximately 48 hours. During this period, it is believed that secondary bonds that were previously formed between protein molecules (collagen-collagen bonds or zein-zein bonds) form between the enzyme and the inactive protein coating (collagen-enzyme bonds or zein-enzyme bonds). However, the exact mechanism by which the enzyme is bound to the filter is not precisely known.

The bond between the enzyme and the inactive protein coating is, however, strong. No chemical reactions that are detrimental to enzyme activity occur during complexing. Thus, an enzyme is firmly bonded to the filter with a minimum loss of activity.

The procedure for complexing the enzyme on to the protein coated filter can vary. In each case, however, the membrane is maintained in an aqueous enzyme-containing solution until complexing occurs. Usually, complexing is complete within a period ranging from 10 hours to 2 days. The temperature range during this time should be maintained within 4° to 20° C, depending upon the particular enzyme used. Maximum enzyme complexing is measured by the activity of the material to which it is bound after washing. Thus, enzyme activity can be used to indicate when complexing is complete. The enzyme containing material is preferably dried at room temperature or below so as not to damage the bound enzyme.

The ability of a zein coated filter to stably immobilize enzymes and the ability of this material to catalyse a reaction for reactants flowing through the pores of the filter ws demonstrated with invertase, DNase and uricase as is set forth in Examples 3, 4 and 5.

EXAMPLE 3

Invertase

Four pieces of zein-invertase complex filters were removed from an invertase solution (12.5 mg/ml crude invertase preparation) and were stacked in series. 25 ml. of 6 percent sucrose solution was passed through the filter by throttling the gravity-induced flow rate, giving an average residence time of 9–24 seconds for each slug of material passing through the stack of filters. The stacks of filters were washed thoroughly with 50 cc of water between each run.

Between runs 4 and 5, the whole reactor was disassembled, each filter was washed thoroughly and reassembled in random order.

EXAMPLE 4

DNase

Six pieces of zein-DNase complexed filter were prepared from a DNase solution of 5 mg/ml and stacked together. The amount of DNase leached out upon distilled water rinse leveled off rapidly as shown below:

| 10cc volume aliquot of distilled water passed through (cc) | Amount of DNase leached out (mg) |
|---|---|
| 10 | 4.20 |
| 20 | 0.90 |
| 30 | 0.40 |
| 40 | 0.12 |
| 50 | 0.01 |
| 60 | — |

A DNA solution (0.82 mg/cc) was then passed through the filter stack. The result is summarized below (no DNA was retained by the filter).

| Flow rate of solution through filter (ml/min) | % Conv. (% of phosphodiester bonds cleaved) |
|---|---|
| 0.250 | 54 |
| 0.167 | 78* |
| 0.250 | 52 |
| 0.250 | 54 |

(*Due to longer residence time)

The filters of the present invention containing bound enzymes have many applications. A few applications for the filters of the present invention are set forth in the following examples.

EXAMPLE 5

Alcoholic Beverages

A. By employing matrix-bound enzymes, the fermentation of glucose to alcohol can be accomplished without the necessity of adding yeast to the system.

B. By using matrix-bound lysozyme and β amylase, yeast can be broken down to the point where there is less tendency for a beverage to clog filters, thus making the economics of beverage filtration more attractive.

EXAMPLE 6

Petroleum/Fuels

A great deal of research has been done on the ability of certain bacteria to metabolize petroleum distillates and convert them to protein. By bonding metabolic enzymes, these reactions can be conducted more economically and efficiently without employing bacteria to produce a new and inexpensive source of food.

EXAMPLE 7

Pharmaceutical/Toiletries

A. By binding an antigen, rather than an enzyme, to a surface, the related human antibody specific for that antigen can be isolated; that is, the antigen will selectively bind the antibody. The antibody can subsequently be released by washing the column with 0.1N potassium iodide or other decomplexing agent, thus recovering a pure antibody for use as a drug or for further study.

B. A matrix-bound antibody can be repeatedly used to isolate the related antigen.

C. By incorporating enzymes such as DNase and RNase into a matrix and by passing a viral (DNA or RNA-based) vaccine through a column, the genetic material contained in the vaccine can be inactivated while maintaining antigenic activity, because the viral proteins will be undamaged.

D. By incorporating lysozyme into an insoluble matrix, suspensions can be clarified routinely and cheaply by lysing the cell walls. Subsequent ultrafiltration or membrane filtration can remove the debris.

EXAMPLE 8

Other Food and Beverages

A. By insolubilizing invertase, the hydrolysis of sucrose to glucose and fructose (inverted sugar) can be catalyzed for beverages and syrup.

B. By hydrolyzing with papain and thus solubilizing certain fish proteins that are presently discarded, economical high-protein beverages can be produced.

EXAMPLE 9

Medical/Clinical

A. Many enzymatic reagents are not being used for routine clinical diagnosis and analytical determinations. By insolubilizing these enzymes, a rapid, reusable system for performing the following clinical tests can be produced.
1. Glucose-6-phosphate dehydrogenase combined with hexokinase can be used to detect glucose by following the NAD-NADH shift. This can be observed spectrophotometrically at a wave length of 340 nanometers.
2. LDH may be detected by using a polarographic enzyme electrode. The bound enzyme is lactate oxidase.
3. The measurements of the concentration of uric acid in blood serum in the manner described in Example 5 with uricase.
4. DPN - diaphorase for LDH measurements.
5. Urease - for urea determinations.

B. Bound enzymes, introduced or encapsulated into the bloodstream can be used to treat enzyme deficiency diseases such as phenylketonuria.

C. Urease can be used to convert urea to $NH_4^+ + HCO_3^-$, thus chemically detoxifying the blood by degrading urea.

In addition to the foregoing applications, there are many other uses for bound enzymes. For example, virtually anybody studying the nature of enzymic reactions would benefit from the insolubilization of the enzymes under question. Furthermore, people who routinely perform biochemical operations involving proteolysis or cell membrane breakdown would benefit from a system containing bound proteinase or lysozyme, respectively. In addition to the foregoing, a person wishing to rapidly perform a complex series of biochemical reactions could connect different bound enzymes in series to greatly facilitate and increase the yield of his reaction scheme.

Of course, membrane bound enzymes in accordance with the present invention have wide application in clinical diagnosis. For example, the use of enzyme assay procedures for the detection of various metabolites in body fluids appears to have become quite popular in recent years. Those enzyme assay procedures which can be advantageously improved with the filter of the present invention include:

1. Detection of blood alcohol using the following scheme:

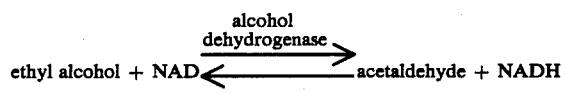

The NAD - NADH shift may be detected spectrophotometrically at 340 nanometers as previously described.

2. Detection of serum lactate for diagnosis of anxiety neuroses:

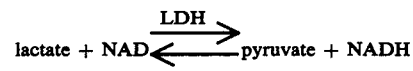

Again the NAD - NADH shift may be detected as described.

The activity of various enzymes (e.g. DNase, invertase) has been demonstrated to be stable over a period of weeks within ± a few percent of its initial value; uricase bound in accordance with the invention has been demonstrated to be stable over a period of 5 months when stored under refrigerated conditions (4° C) and used at room temperature. No upper limit on the period of stability has been observed. The acitivity is assayed by merely passing the substrate at a constant flow rate through the pores of the membrane filter-enzyme complex, and assaying for activity as indicated by conversion of substrate → product.

An important embodiment of the present invention is an enzyme column containing an active membrane material. Such a column is shown in FIGS. 1-5 and includes a cuvette 60, a lower column segment 62 and an upper column segment 64. The column 66 is dimensioned so that it can be placed in a centrifuge. The cuvette 60, and segments 62 and 64 are molded out of a transparent plastic material such as polystyrene. The lower ends of segments 62 and 64 are fitted with support rings 68 and 70 respectively. The support rings 68 and 70 have two functions. They provide a means for coupling the cuvette 60 to the lower segment 62 and the lower segment 62 to the upper segment 64. They also position filter membranes 72 and 74. As is explained in greater detail below, prefilter 72 is a membrane filter having an average pore size of 0.45 microns and filter 74 is a membrane which has been impregnated with an enzyme in accordance with the present invention. The purpose of prefilter 72 is to prevent filter 74 from clogging.

As is shown in FIG. 1, the upper portions of the cuvette and lower column segment is provided with a vent 80 and 82 respectively. The inclusion of the vent below the filter has been found to be advantageous in producing the proper flow of filtrate through the filter. Upper column segment 64 is also shown to have a vent 84. The reason for including a vent on the upper column segment is so that it can be interchanged for a lower column segment. Since there is no filter above vent 84, it serves no purpose other than rendering the upper column segment interchangeable with the lower column segment. The column segments are also provided with shoulders into which teflon gaskets 86 and 88 fit. At this point it should be noted that in the drawing a single filter 74 is shown below the lower column segment. As will be more apparent from the discussion which follows, it is advantageous to include a stack of biologically active filters to increase the residence time of the sample flowing through filter 74. For simplicity, however, only one active filter 74 is shown in the drawing.

Analyses in which an enzyme column in accordance with the present invention are used, are those that measure the total change between end points. For instance, if the substance $\alpha$ is to be determined and it can be converted into $\beta$ in the enzymatic reaction $\alpha \rightarrow \beta$; and $\alpha$ and $\beta$ have different characteristic absorption spectra; then, the difference in optical absorbance at a particular wave length between a sample reacted with an enzyme and an unreacted sample becomes a measure of the $\alpha$ concentration originally present. In this kind of measurement, the residence time is sufficient for the reaction to reach for completion.

One important use for an enzyme column in accordance with the present invention is in the analysis of uric acid in blood serum by reacting the uric acid with the enzyme uricase. The reaction upon which the analysis depends is as follows:

Uric acid $\xrightarrow{Uricase}$ Allantoin

In this reaction, uric acid is an ultraviolet absorbing material or chromogen and it contributes to a high optical density system at the start of the reaction. The optical density decreases as the reaction proceeds to the right. The uric acid absorbs light with wavebands having an optical center at 292 nm. Thus, the amount of uric acid is determined by comparing the optical absorption of such light by an unreacted sample with the absorption of an identical aliquot reacted with a known amount of uricase. From the difference in absorition between the two aliquots, the amount of uric acid can be calculated. This analysis is further illustrated by the following example.

EXAMPLE 10

URIC ACID DETERMINATION WITH AN ENZYME COLUMN

A. PREPARATION OF ZEIN FILTER

1. Treatments of impregnated filter and column prefilter:

The filters employed are 13 mm "SS" Millipore filters. To wash out any leachable materials that absorb at 292 nm., distilled water may be passed through the substrate filter until the increment of effluent peak optical density is close to that of the original distilled water. The rinsed filters are then air dried.

2. Preparation of Zein Filters:

The filter to be impregnated with uricase is first coated with zein by procedure set forth in example 1.

3. Treatments of Zein filter before complexing with enzyme:

Repeat step 1 above. Rinse the Zein filter with distilled water until the Δ O.D. at 280 nm. is within 0.01 relative to distilled water. The filter is then again air dried at room temperature.

B. Procedure for Preparation of Enzyme Columns

APPARATUS

1. A 10 ml beaker, thoroughly washed, rinsed with distilled water and dried — for each set of three — 13 mm columns to be prepared.
2. Parafilm squares.
3. Clean, dry test tubes, rinsed as above, for preparation of enzyme solution ($\sim$ 10 mm diameter).
4. Sigma uricase from Candida Utilis, sigma catalog number U-8500, specific activity 2.5 - 6.5 units 1 mg.
5. Crushed ice (finely crushed with blender) and tray for ice-water bath to contain enzyme solution and complexing beakers.

PROCEDURE

1. Weigh out, on a glassine paper about 2.5 inches square, 0.5 mg enzyme per column to be prepared (i.e., if making ten columns weigh out 5 mg. enzyme).
2. Add to a single test tube on ice, 200 $\lambda$ distilled water per column to be prepared. Bring test tube contents down to 0° C before performing next step.
3. Quantitatively transfer enzyme to distilled water to yield a 2.5 mg. ml solution. Stir thoroughly until dissolved.
4. Add 600 ml enzyme solution to each 10 ml beaker, while on ice. Beaker should have been sitting in crushed ice for at least 10 minutes before addition of enzyme to thoroughly chill beaker walls.
5. To each beaker, add, in series, 32 pieces of 13 mm Zein filters. Allow enzyme solution to thoroughly wick up through each filter. Keep beaker covered with Parafilm when not manipulated. Beaker should always be on ice.
6. When wicking is completed, see that stack of filters are in intimate contact with one another. Cap beaker tightly with parafilm, wrap with tape. Store at 2° - 4° C for at least 24 hours.
7. After a minimum of 24 hours (48 is preferred), remove cover of beaker, spread filters out on clean, absorbent lint free tissues in a petri dish, and dry under mild dessication (i.e. leave petri dish loosely capped in presence of dessicant) in refrigerator.

THE FOLLOWING STEPS MAY BE PERFORMED AT ROOM TEMPERATURE

8.

A. Prepare 0.01N borate buffer, pH 8.2 as described on on page J - 195 of the 1968 Sober edition of The Handbook of Biochemistry which is published by the Chemical Rubber Company. Wet filters with buffer.

B. Load each section of the tubes of FIGS. 1-5 with:
 1. Upper segment 64
   a. 1 — teflon gasket 86
   b. 1 — prerinsed prefilter 72 of the type described above prewet with buffer
 2. Lower segment 62
   c. teflon gasket 88
   d. 12 — uricase Zein filters 74 as prepared above.

ENZYME COLUMN CONDITIONING

Rinse both columns with 40 cc. of borate buffer under vacuum. This "conditions" the column. The column should be stored, after conditioning at 2° to 4° C until used.

ANALYSIS

The uric acid enzymatic assay tube utilizes two columns, the enzyme column and the reference column. The reference column is identical to the enzyme column except that the reference column contains no enzyme. Equal amounts of diluted serum samples are placed into the prefilter segment of each column. The centrifugal force will pull the samples through the prefilters, through the enzyme or reference segment and into the cuvettes.

The enzyme segment contains a stack of filters with uricase bound to it. Because of the high surface to volume ratio of the stacked porous matrices there is ample uricase bound to the surface to ensure the completion of the conversion of uric acid into allantoin before the sample enters into the cuvette segment. Furthermore, the uricase physically remains in the enzyme segment so that segment can be used again and again. Since there is no uricase in the reference segment, the uric acid of the sample in the reference column remains unchanged. The prefilter segment removes any particles in samples which may clog the enzyme or reference segment. It must be replaced periodically. Both the prefilter segment and cuvette are disposable units.

A minimum contact time (residence time) between sample and enzyme matrix is a necessity in order to have the complete conversion of uric acid. This can be achieved by setting the centrifuge rotation speed in the 1000 RPM region to give 200 g of relative centrifugal force.

For most tabletop clinical centrifuges, it is recommended to start from the lowest rotation speed and if at the end of six minutes (nominal process time) all of the buffer solution has not passed from the top compartment into the cuvette, the rotation speed setting position shall be advanced to the next higher speed position such that the process time required is less than 6 minutes but not less than 3 minutes.

OPERATION PROCEDURES

1. Set up columns by putting prefilter segment above the enzyme or reference segment, and the cuvette segment below the enzyme or reference segment such that the enzyme or reference segment is in the middle. The overall length of each column is equivalent to a 15ml conical centrifuge tube.
2. Turn on a spectrophotometer. Set wavelength at 292nm.
3. Dilute 0.2ml of serum sample with 5.8ml of buffer.
4. Add 2.8ml of diluted serum sample to prefilter segment in each of the two columns. Place the pair of tubes into centrifuge head in opposite positions.
5. Centrifuge the tubes at above selected rotation speed for 6 minutes.
6. Transfer the samples to a container and measure the optical density (O.D.) of the samples at 292nm.
    For Single Beam measurement:
    a. Set the O.D. of sample from reference thimble at 0.4.
    b. Measure the O.D. of sample from the enzyme column, $D_l$.

For Double Beam measurement:
    a. Make sure that the sample containers are a matched pair.
    b. Put the container containing sample from enzyme cuvette in reference position, the container containing sample from reference cuvette in sample position.
    c. Take the optical density reading, $\Delta$O.D.
7. Calculate the concentration of uric acid by the following relations:
    For Single Beam measurement:

$$\text{uric acid (mg\%)} = (0.4 - D_l) \times 42.5$$

For Double Beam measurement:

$$\text{uric acid (mg\%)} = \Delta O.D. \times 42.5$$

8. Before the columns are re-stored in the refrigerator at 4° C, they must be flushed with buffer by adding 3ml of buffer to top compartment of each tube. Centrifuge the tubes for 5 minutes.

There are several significant advantages which derive from using an enzyme column in accordance with the present invention. One advantage is that special tests which are difficult to perform with other systems become possible. In this regard it should be noted that the enzyme column is not limited to the uric acid analysis. Indeed, many enzymatic analyses can be advantageously run with an enzyme column in accordance with the present invention. An example of an analysis which can be run more conveniently with enzyme column of the present invention is the analysis of glucose using the reactions heretofore described.

The enzyme column is particularly advantageous for performing stat tests. Analysis for uric acid with the enzyme column can be run in 6–7 minutes, as compared to 30 minutes using prior art systems. Of course, the fundamental advantage of the bound enzyme method is its specificity and the reuseibility of the bound enzymes.

A further use of a urease membrane in accordance with the present invention is for the measurement of urea. For a discussion of this process, see the article entitled, "Enzymes Bound to Artificial Matrixes," by Klaus Mosbach, *Scientific American*, March, 1971, pp. 26–33, the teachings of which are incorporated herein by reference. On page 32 of this Scientific American article, the measurement of urea utilizing a urease-containing gel is disclosed. In accordance with the present invention, urease is bound to a porous polymeric membrane and substituted for the urease-containing gel disclosed in the *Scientific American* article.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A composite membrane structure for immobilizing biologically active proteinaceous materials comprising a thin microporous membrane having capillary pore sizes in the range from about 25 nanometers to 14 micrometers, said membrane being formed from a biologically inert synthetic polymer, said membrane having a thin, water-insoluble coating of an inert proteinaceous material on its surfaces, said coating being formed by (a), soaking the membrane with a solution of the proteinaceous material in an organic solvent, and (b), drying to form a thin layer of said inert proteinaceous material such that the coated membrane retains its intercommunicating capillary pores that extend through its structure, to permit fluid flow therethrough, and that provide a high surface-to-volume ratio, said coated membrane being capable of stably immobilizing a biologically active proteinaceous material thereon with retention of its activity upon contacting the coated membrane with a solution in which the biologically active material is dissolved, and drying.

2. A composite membrane in accordance with claim 1 wherein the inert proteinaceous material forming the coating is a natural protein.

3. A composite membrane in accordance with claim 1 wherein the inert proteinaceous material forming the coating is a synthetic polypeptide.

4. A composite membrane structure in accordance with claim 1 wherein the inert proteinaceous material forming the coating is zein or collagen.

5. A composite membrane in accordance with claim 1 having a biologically active proteinaceous material immobilized thereon.

6. A composite membrane in accordance with claim 4, having an enzyme immobilized thereon.

7. A composite membrane in accordance with claim 4, having an antibody immobilized thereon.

8. A composite membrane in accordance with claim 4, having an antigen immobilized thereon.

9. A method for performing an analysis comprising:
selecting a sample suspected of containing a substance in solution to be analyzed for, contacting the sample with said membrane having a biologically active proteinaceous material immobilized thereon in accordance with claim 5, and
thereafter determining whether a reaction occurs between the immobilized proteinaceous material and said substance, which reaction indicates the presence of said substance.

10. A method in accordance with claim 9 wherein the sample is to be analyzed for a substance in solution that is known to change in optical density upon reaction with said immobilized biologically active proteinaceous material, and wherein the step of determining whether a reaction occurred includes measuring the optical density to determine any change that would indicate whether the sample contained the substance in question.

11. A process in accordance with claim 10 wherein the immobilized biologically active material is an enzyme.

12. A process in accordance with claim 11 wherein the substance that is known to change in optical density upon reaction is uric acid, and the immobilized biologically active proteinaceous material is the enzyme uricase.

13. An analytical device comprising a composite membrane structure, having a biologically active proteinaceous material immobilized thereon in accordance with claim 5 said structure being mounted in a holder, a sample chamber disposed in the holder on one side of the composite membrane structure, and a filtrate chamber disposed on the other side of the composite membrane structure.

14. An analytical device in accordance with claim 13 wherein the holder, the membrane and the coating on the membrane are substantially inert relative to the biologically active proteinaceous material that is immobilized on the composite membrane structure.

15. An analytical device comprising:
a cuvette;
a column segment mounted on the upper end of the cuvette, said column segment and cuvette having a configuration permitting the assembly thereof to be placed in a centrifuge, and
a composite membrane structure having a biologically active proteinaceous material immobilized thereon in accordance with claim 5 disposed across the flow path between the column segment and the cuvette.

16. An analytical device in accordance with claim 15 wherein the coating is formed from zein and the immobilized biologically active material is the enzyme uricase.

17. A method for bringing about a molecular interaction between a first proteinaceous material that is biologically active and a second substance that either binds with or is catalytically changed by the first material, comprising:
immobilizing the first material on a composite membrane structure in accordance with claim 1, and
passing a solution of the second material through the composite membrane structure on which the first material is immobilized, to permit binding or a catalytic change to occur.

18. A method in accordance with claim 17 wherein the immobilized first material is an enzyme.

* * * * *